United States Patent [19]
Yoneda et al.

[11] Patent Number: 5,993,817
[45] Date of Patent: Nov. 30, 1999

[54] METHOD TO AMELIORATE OSTEOLYSIS AND METASTASIS

[75] Inventors: Toshiyuki Yoneda; Gregory R. Mundy; Theresa A. Guise, all of San Antonio, Tex.

[73] Assignee: Xenotech, Foster City, Calif.

[21] Appl. No.: 08/386,361

[22] Filed: Feb. 9, 1995

Related U.S. Application Data

[63] Continuation-in-part of application No. 08/376,359, Jan. 23, 1995, Pat. No. 5,626,845.

[51] Int. Cl.$^6$ .......................... A61K 39/395; C07K 16/18; C07K 16/22; C07K 16/26

[52] U.S. Cl. ...................... 424/158.1; 424/145.1; 424/156.1; 424/138.1; 424/155.1; 530/387.1; 530/388.24; 530/389.2; 530/387.7; 530/388.8; 530/388.85

[58] Field of Search .......................... 424/145.1, 130.1, 424/138.1, 155.1, 158.1, 156.1; 530/388.7, 387.1, 388.24, 389.2, 388.8, 388.85, 389.7

[56] References Cited

U.S. PATENT DOCUMENTS

| | | | |
|---|---|---|---|
| 5,114,843 | 5/1992 | Rosenblatt et al. | 435/7.21 |
| 5,116,952 | 5/1992 | Martin et al. | 530/399 |
| 5,217,896 | 6/1993 | Kramer et al. | 435/240.27 |
| 5,312,810 | 5/1994 | Wood et al. | 514/12 |

FOREIGN PATENT DOCUMENTS

WO 91/10741    7/1991    WIPO ........................ C12P 21/06

OTHER PUBLICATIONS

Tashjian, A.H. et al., "Immunochemical identification of parathyroid hormone in non–parathyroid neoplasms associatd with hypercalcemia," *J. Exp. Med.*, 119:467–484 (1994).

Kohler, G. and Mislstein, C., "Continuous cultures of fused cells secreting antibody of predefined specificity," *Nature*, 256:495–497 (Aug. 1975).

Kohler, G. and Milstein, C., "Derivation of specific antibody–producing tissue culture and tumor lines by cell fusion," *Eur. J. Immunol.*, 6:511–519 (1976).

Eilon, G. and Mundy, G.R., Direct resorption of bone by human breast cancer cells in vitro, *Nature*, 276:726–728 (Dec. 1978).

Horiuchi et al., "Similarity of synthetic peptide from human tumor to parathyroid hormone in vivo and in vitro," *Science*, 238:1566–1568 (Dec. 1987).

Suva et al., "A parathyroid hormone–related protein implicated in malignant hypercalcemia: Cloning and expression," *Science*, 237:893–896, (Aug. 1987).

Yates et al., "Effects of a synthetic peptide of a parathyroid hormone–related protein on calcium homeostasis, renal tubular calcium reabsorption, and bone metabolism in vivo and in vitro in rodents," *J. Clin. Invest.*, 81:932–938 (Mar. 1988).

Gregory R. Mundy, "Hypercalcemia of malignancy revisited," *J. Clin. Invest.*, 82:1–6 (Jul. 1988).

Kukreja, S.C. et al., "Antibodies to parathyroid hormone–related protein lower serum calcium in athymic mouse models of malignancy–associated hypercalcemia due to human tumors," *J. Clin. Invest.*, 82:1798–1802 (Oct. 1988).

Southby et al., "Immunohistochemical localization of parathyroid hormone–related protein in human breast cancer," *Cancer Res.*, 50:7710–7716 (Oct. 1990).

Burton et al., "Parathyroid hormone related peptide can function as an autocrine growth factor in human renal cell carcinoma," *Biochem. Biophys. Res. Comm.*, 167(3):1134–1138 (Mar. 1990).

Lawrence E. Mallette, "The parathyroid polyhormones: New concepts in the spectrum of peptide hormone action," *Endocrine Rev.*, 12(2):110–117 (Feb. 1991).

Powell et al., "Localization of parathyroid hormone–related protein in breast cancer metastases: Increased incidence in bone compared with other sites," *Cancer Res.*, 51(11):3059–3061 (Jun. 1991).

Yoneda et al., "Occurrence of hypercalcemia and leukocytosis with cachexia in a human squamous cell carcinoma of the maxilla in athymic nude mice: a novel experimental model of three concomitant paraneoplastic syndromes," *J. Clin. Oncol.*, 9(3):468–477 (Mar. 1991).

Abou–Samra et al., "Expression cloning of a common receptor for parathyroid hormone and parathyroid hormone–related peptide from rat osteoblast–like cells: A single receptor stimulates intracellular accumulation of both cAMP and inositol trisphosphates and increases intracellular free calcium," *Proc. Natl. Acad. Sci. USA*, 89:2732–2736 (Apr. 1992).

Nakai et al., "A synthetic antagonist to laminin inhibits the formation of osteolytic metastases by human malanoma cells in nude mice," *Cancer Res.*, 52:5395–5399 (Oct. 1992).

Sato et al., "Passive immunization with anti–parathyroid hormone–related protein monoclonal antibody markedly prolongs survival time of hypercalcemic nude mice bearing transplanted human PTHrP–producing tumors," *J. Bone Min. Res.*, 8(7):849–860 (Jul. 1993).

Kohno et al., "The expression of parathyroid hormone–related protein in human breast cancer with skeletal metastases," *Surgery Today. Japan J. Surg.* 4:215–220 (1993).

Sasaki et al., "Osteolysis and tumor growth are enhanced in sites of increased bone turnover in vivo," *J. Bone Min. Res.* 9(11):s194 (Nov. 1994).

(List continued on next page.)

*Primary Examiner*—Nancy A. Johnson
*Attorney, Agent, or Firm*—Bozicevic,Field & Francis LLP; Bret Field

[57] ABSTRACT

Materials immunoreactive with parathyroid hormone-related protein (PTH-rp) are used in the invention method to prevent and treat cancer metastasis to bone and cancer cell growth in bone as well as osteolysis and symptomatic sequelae thereof. Antibodies with human characteristics are included in the invention for application of the invention method to human subjects.

8 Claims, 3 Drawing Sheets

OTHER PUBLICATIONS

Li et al., "Growth factor–like properties of parathyroid hormone–related peptide in transfected rodent cell lines," *Cancer Res.*, 53(13):2980–2986 (Jul. 1993).

Sasaki et al., "Growth of metastatic cancer in bone is impaired by inhibitors of bone resorption in vivo," *J. Bone Min. Res.*, 8(1):s139 (Aug. 1993).

Yoneda et al., "Development of a model of a human tumor which causes metastatic bone lesions which are mixed osteolytic and osteoblastic," *J. Bone Min. Res.*, 9(11):s293 (Nov. 1994) (Abstract).

Guise et al., "Parathyroid hormone–related protein (PTHrP) expression by breast cancer cells enhance osteolytic bone metastases in vivo," *J. Bone Min. Res.*, 9(11):s128 (Nov. 1994).

Gilles et al., "Cytokines stimulate interleukin–6 production in bone to a much greater extent then systemic factors," *J. Bone Min. Res.*, 9(11):s337 (Nov. 1994).

Kukreja Endocrinology 127:305–310 1990.

Seaver Gen Eng News 14(14):10 and 21. 1994.

McClellan Endocrinology 131:2263 1992.

Oshima, Pept. Chem pp. 547–9 1992.

Harrison's "Principles of Internal Medicine" $12^{th}$ edition pp. 1938–1941, 1991.

METHOD TO AMELIORATE OSTEOLYSIS AND METASTASIS

This is a Continuation-in-Part of U.S. Ser. No. 08/376,359, filed Jan. 23, 1995 now U.S. Pat. No. 5,626,845.

TECHNICAL FIELD

The invention relates to the prevention and treatment of cancer metastasis to bone and bone cancer growth and to associated osteolysis, some of the most problematic aspects of cancers of many origins. More specifically, the invention concerns use of antibodies to parathyroid hormone-related protein (PTH-rp) and other forms of anti-PTH-rp to alleviate these conditions.

BACKGROUND ART

It has long been understood that morbidity and mortality caused by cancer, especially in view of the fact that surgical techniques are readily available, are due to more-or-less systemic sequelae of the original multiplication of the cancer cells. Metastasis of an original tumor to additional locations, the destruction of target locations as a direct or indirect result of this metastasis, cachexia, hypercalcemia, and other symptomologies characterize the course of the malignancy. The mechanisms whereby these sequelae occur are believed to involve a variety of cytokines, growth factors, and cell adhesion molecules, among other factors. It is entirely unknown, however, how cancers dissolve bone in bone metastases since at present, the only cells known to be able to dissolve bone are osteoclasts. It is not known how metastasized cancer dissolves bone in order to accommodate the growth of the cancer.

One of many factors which is known to play a role in at least some of these processes is parathyroid hormone-related protein (PTH-rp). Due to its similarity to PTH, it has been recognized as a mediator of humoral hypercalcemia of malignancy (HHM). In this role, PTH-rp secreted by the tumor is circulated through the blood and is associated with hypercalcemia, an index of bone resorption. PTH-rp has been shown to be the cause of systemic bone resorption and calcium reabsorption from urine at the tubule. Both of these result in a systemic elevation of blood calcium levels. This factor has been described in connection with HHM in U.S. Pat. No. 5,116,952. This patent also describes preparation of anti-PTH-rp antibodies using peptide subunits of the partially sequenced protein. This protein has also been called adenylate cyclase stimulating factor (ACSF) in U.S. Pat. No. 5,312,810 and humoral hypercalcemic factor (hHCF) in U.S. Pat. No. 5,114,843. The association of PTH-rp with HHM is also described by Yates, A. J. P. et al., *J Clin Invest* (1988) 81:932–938. Japanese application A4-228089, published Aug. 18, 1992 describes recombinant production of anti-PTH-rp antibodies, including murine/human chimeras. This application also discloses animal studies demonstrating that either murine or chimeric monoclonal antibodies directed to PTH-rp ameliorate the effects of HHM in a model system where HHM is caused by either systemically infusing PTH-rp into mice peritoneally or by implanting PTH-rp-producing prostate cancer cell lines in nude mice.

PTH-rp has been purified from human lung cancer, breast cancer and renal cell carcinoma. Although PTH-rp was originally found associated with tumor cells, it is also present widely in normal tissue. The gene encoding PTH-rp was cloned and expressed by Suva, L. J. et al. *Science* (1987) 237:893–895. PTH-rp has been shown to bind to PTH receptors (Abou-Samra, A. et al. *Proc Natl Acad Sci USA* (1992) 89:2732–2736) and has activities similar to PTH (Horiuchi, N. et al. *Science* (1987) 23:1566–1568). It has been shown to stimulate adenylate cyclase in renal and bone systems, increase tubular reabsorption of calcium, decrease renal phosphate uptake and stimulate 1α-hydroxylase. Thus, it is logical that where PTH-rp is circulating, inhibitors of the PTH-like action of PTH-rp would interfere with these biological events, including calcium reabsorption from urine to blood at the kidney tubules and systemic bone resorption. However, PTH/PTH-rp receptors are not found on osteoclasts. Either such receptors have been resistant to characterization or to the extent that PTH-rp may be found to affect osteoclasts, the effect may be exerted by some unknown mechanism, for example by effecting the secretion of unknown mediators from osteoblasts (which are known to have PTH/PTH-rp receptors). There is no available evidence to connect PTH-rp to bone resorption mediated by osteoclasts.

PTH-rp also has properties that are not shared by PTH, including regulation of placental calcium transport as summarized in a review by Mallette, L. E. *Endocrine Rev* (1991) 12:110–117. Of particular relevance with respect to the invention herein is that PTH-rp has also been associated with the establishment of bone metastasis in breast cancer (Powell, G. J. *Cancer Res* (1991) 51:3059–3061; Southby, J. et al. *Cancer Res* (1990) 50:7710–7716). The data provided in these disclosures show only the association of PTH-rp with bone metastasis of breast cancer, but no causal relationships are implied. PTH-rp has been considered as a possible autocrine factor for a limited number of tumors (Burton, P. B. J. et al. *Biochem Biophys Res Com* (1990) 167:1134–1138; Li, X. et al. *Cancer Res* (1993) 53:2980–2986).

Thus, the precise role of PTH-rp in mediating the effects of a primary cancer is not well understood. Not only are there additional factors which also participate in the progress of this condition, the production of PTH-rp is believed affected by additional factors such as prolactin, glucocorticoids, epidermal growth factor, TGF-α, TGF-β, estrogen, "stretch," and even extracellular calcium concentration. The presence of additional factors is particularly important and adds to the uncertainty of the mechanism. Factors such as IL-1, IL-6, IL-11, M-CSF and GM-CSF in particular have been considered important in bone resorption. In a report by Sasaki, A. et al. *J Bone Min Res* (1994) 9 *Supp* 1:S 294, B 257, it is demonstrated that administration of recombinant human IL-1α into calvaria of nude mice attracted metastasis of cancer calls that had been inoculated into the left ventricle, while other bones of the same animal which did not receive IL-1α did not show cancer metastasis. Gilles, J. et al. ibid. S 337, B 433, suggest that IL-6 markedly potentiates the effects of bone resorbing factors on osteoclastic bone resorption and that IL-6 production in bone is important both in cytokine-mediated bone resorption and in those disease states where cytokine-mediated bone resorption is potentially involved, such as estrogen-related bone loss, myeloma and Paget's Disease. It has also been shown that transgenic mice that are modified to comprise an IL-6 gene knockout show reduced bone loss in models for osteoporosis. It has been confirmed that osteoclasts have receptors for IL-6 and IL-11. Osteoclasts treated with M-CSF and GM-CSF show accelerated maturation in culture. Transgenic mice that have genetic deficiencies in the M-CSF gene also exhibit a condition mimicking osteoporosis and this condition can be treated by injection of M-CSF. Thus, a multiplicity of factors are known which appear to play a major role in local bone resorption and/or osteoclast activation.

Sato, K. et al. *J Bone Min Res* (1993) 8:849–860 describe results obtained in a murine model of HHM wherein the affected mice were administered a monoclonal murine antibody obtained from immortalized spleen cells of mice injected with a peptide representing amino acid positions 1–34 of PTH-rp. Passive immunization resulted in decreases in serum calcium concentration in these hypercalcemic nude mice that had been transplanted with human PTH-rp-producing tumors. These tumors were implanted in nonbone tissue to provide a model for HHM. The authors suggest that if a human counterpart to this antibody could be obtained, it might be used in treatment where malignancy-associated hypercalcemia is due to PTH-rp. (Sato, K. et al. use the term "malignancy-associated hypercalcemia" in this paper; it is synonymous with HHM.) In this model, elevated levels of PTH-rp are maintained in the blood which are, evidently, mitigated by the administration of anti-PTH-rp antibodies. Similar studies were conducted by Kukreja, S. C. *J Clin Invest* (1988) 82:1798–1802 and showed that polyclonal anti-PTH-rp antibodies suppress hypercalcemia in a human tumor model of HHM. This is the first disclosure of any therapeutic effect of anti-PTH-rp on HHM. The relevance of this model is verified by the finding of Tashjian, A. H. et al. *J Exp Med* (1964) 119:467 that 15% of 147 hypercalcemic breast cancer patients exhibited no bone metastases.

Hypercalcemia may also be caused by osteolysis of bone through the mediation of osteoclasts. Mundy, G. R. *J Clin Invest* (1988) 82:1–6 describes increased osteoclastic bone resorption in areas surrounding breast cancer metastases. In addition, breast cancer cells have been shown to resorb bone directly in vitro (Eilon, G. & Mundy G. R., *Nature* (1978) 276:726–728.

Kohno, N. et al. *Surgery Today, Japan J Surg* (1993) 4:215–220 reported studies performed on immobilized sections of surgically removed breast cancers using an anti-PTH-rp antibody also prepared by immunizing mice with the first 34 amino acids of PTH-rp. The antibody bound to 57% of the tumors; it bound to 83% of the tumors derived from patients who developed skeletal metastases but only 38% in those who either developed lung metastases or no metastases at all. These authors conclude that their results suggest that PTH-rp-positive tumors have an affinity to bone. However, the observations related only to the staining of cancer tissues by anti-PTH-rp and are not quantitative. Thus, the results do not show a causal relationship between the presence of PTH-rp and any acceleration of bone metastasis or growth enhancers. An equally plausible explanation is that PTH-rp is an effect rather than a cause of metastasis, cancer growth and/or osteolysis.

The present inventors have developed a model of human breast cell cancer metastasis to bone that results in osteolysis. Nakai, M. et al. *Cancer Res* (1992) 52:5395–5399; Sasakai, A. et al. *J Bone Min Res* (1993) 8 (*Supp* 1):No. 92. Tumor cells introduced into the left cardiac ventricle of nude mice can be shown to cause osteolytic lesions that can be seen by x-ray examination and that can be confirmed histologically. A375 melanoma cells and the human breast cancer cell line MDA231 have been used in this model. Using this model, it was demonstrated that bone metastasis could be prevented by a synthetic antagonist to laminin.

This model has also been used to demonstrate in vivo the metastatic nature of human neuroblastoma cells as described in an abstract by Yoneda, T. et al. *J Bone Min Res* (1994) 9 (*Supp* 1):S 293, B 225. Six weeks after inoculation with the neuroblastoma cells, x-rays showed lesions in the tibiae that were both osteolytic and osteoblastic, but there was no hypercalcemia or cachexia. Thus, cancer metastasis of the bone is clearly a complex situation which can generate both osteoblasts and osteoclasts and is not always associated with systemic disorders such as hypercalcemia or cachexia. Histologic examination showed that neuroblastoma cells occupied the bone marrow cavity, and there were numerous bone resorbing osteoclasts (which have not been demonstrated to exhibit PTH/PTH-rp receptors) on endosteal bone surfaces. Culture supernatants of the tumor cells stimulated bone resorption in organ cultures of fetal rat long bones and increased proliferation of osteoblastic osteosarcoma cells, which promote bone formation. The culture media contained significant levels of PTH-rp and high levels of IL-6. It is known that osteoclasts have IL-6 receptors.

The present inventors have also demonstrated that the number of osteolytic lesions is increased by enhancing PTH-rp expression of the MDA231 cells used in the model, but not diminished by MDA231 cells transfected with an antisense PTH-rp construct. Overexpressing clones were obtained by transfecting MDA231 cells with cDNA encoding human prepro PTH-rp; clones having diminished production of this peptide were obtained by transfecting the cell line with an antisense construct. A clone showing elevated PTH-rp expression (100 pM/24 hours) produced 16.3±3.8 lesions radiographically at 3 weeks as compared with the antisense construct which secreted less than 0.3 pM/24 hours which produced only 7.6±0.22 lesions. The number of lesions in mice administered unmodified MDA231 cells which produce 1.6–8.4 pM/24 hours PTH-rp is similar to the number of lesions in mice administered the MDA231 cells modified to contain the antisense construct, which produces less PTH-rp. No plasma concentrations of PTH-rp were detectable in any of the mice used in these studies; hypercalcemia was minimal and present only in mice harboring the PTH-rp-enhanced MDA231 cells. The present inventors have also shown that PTH-rp concentrations in serum-free media conditioned by MDA231 cells were increased twofold when the cells were cultured on an extracellular matrix produced by bone cells. These results were reported by Guise, T. A. et al. *J Bone Min Res* (1994) 9 (*Supp* 1):S 128, No. 30.

It has now been found that antibodies specific for PTH-rp are affective in inhibiting metastasis and ameliorating the effects of malignant cells localized in bone. This provides an effective pharmacological approach to treatment.

DISCLOSURE OF THE INVENTION

The invention provides a means to treat localized bone effects of metastasized cancer cells, cancers of bone origin, and osteolytic processes in general characterized by localized concentrations of PTH-rp. By administering materials that are immunoreactive with PTH-rp, metastases to the bone can be prevented, growth of cancer cells present in bone can be inhibited, and osteolytic effects can be prevented and treated. Further, the secondary effects of the metastasis, growth, and osteolysis associated with localized phenomena in bone can be mitigated.

Thus, in one aspect, the invention is directed to a method to treat or prevent metastasis of cancer cells to bone and/or growth of metastasized or bone-originated cancer cells in or on bone, which method comprises administering to a subject in need of such treatment an amount of anti-PTH-rp sufficient to treat or prevent said metastasis and/or growth.

In another aspect, the invention is directed to a method to inhibit osteolysis effected by metastasis of cancer cells to bone and/or growth of metastasized or bone-originated cancer cells in or on bone which method comprises administering to a subject in need of such treatment an amount of anti-PTH-rp sufficient to effect said inhibition.

In still another aspect, the invention is directed to a method to inhibit osteolysis mediated by bone-localized production of parathyroid hormone-related protein (PTH-rp) which method comprises administering to a subject in need of such treatment an amount of anti-PTH-rp sufficient to effect said inhibition. This method is particularly important in instances of osteoporosis, osteomalacia, renal osteodystrophy or Paget's Disease.

Another effect of the method of the invention in attacking the primary targets described above is the amelioration of secondary symptomologies. These include pain, neural compression which may result in paraplegia or paralysis, hypercalcemia, risk of pathologic fractures, cachexia and decreased survival prognosis.

In still other aspects, the invention is directed to compositions useful in the methods of the invention and to methods to identify and treat subjects who would benefit from the methods of invention treatment, as well as methods to obtain antibodies useful in the methods of the invention.

MODES OF CARRYING OUT THE INVENTION

Figure 1:
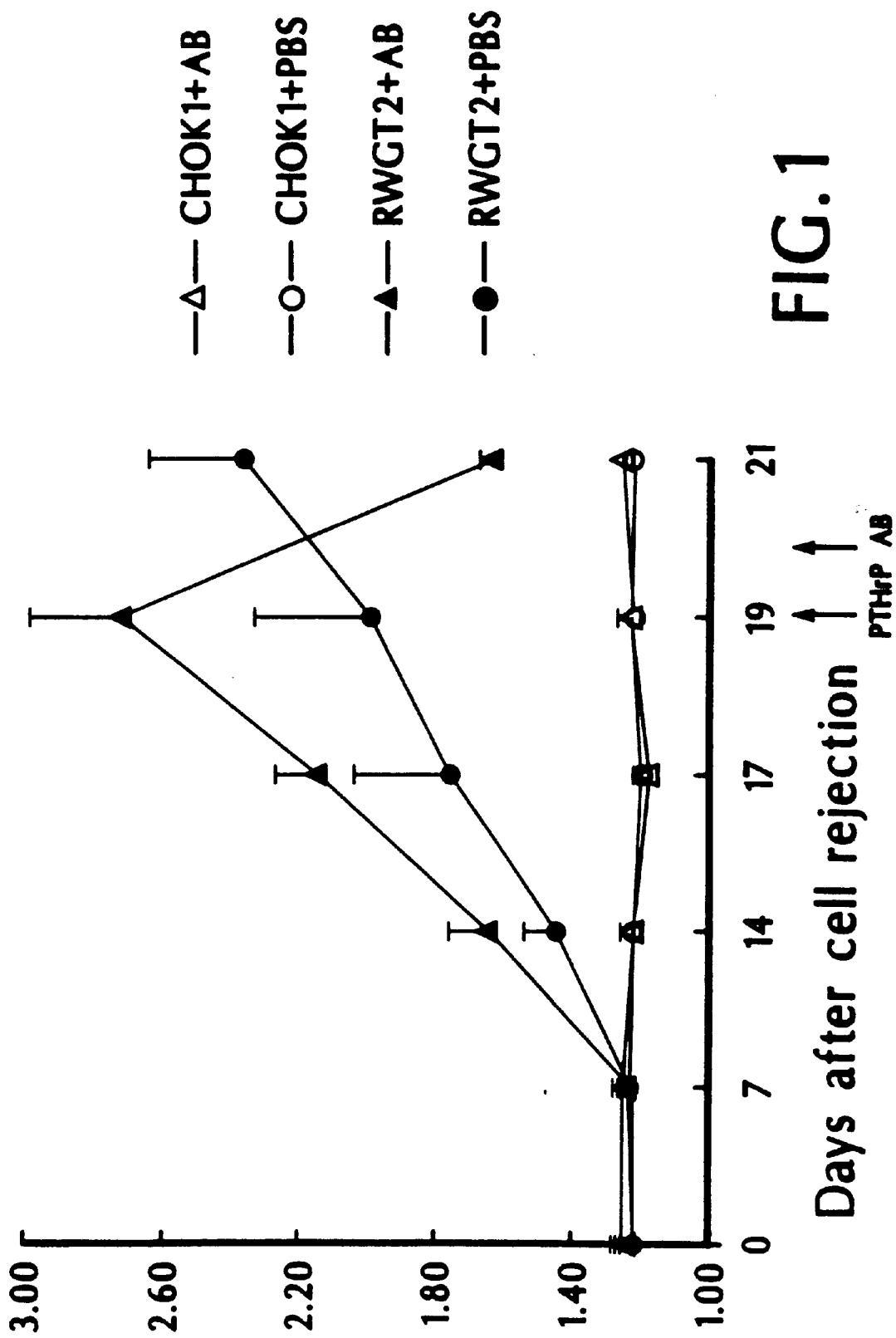
FIG. 1 is a graph that shows the effect of monoclonal antibodies specific for PTH-rp on serum calcium levels in tumor-bearing mice.

All of the invention methods and compositions employ substances immunoreactive or immunospecific for PTH-rp. Substances that are immunoreactive with PTH-rp are generally designated "anti-PTH-rp."

As used herein, the term "anti-PTH-rp" refers to antibodies immunoreactive with PTH-rp and antibody analogs, substitutes and fragments as are known in the art. It is preferred that the anti-PTH-rp also be immunospecific—i.e., not substantially cross-reactive with related materials such as PTH. However, anti-PTH-rp is effective in the method of the invention as long as it is immunoreactive with PTH-rp per se.

Examples of art-known analogs, fragments and substitutes for antibodies include fragments such as Fab, Fab', and F(ab')$_2$ fragments as well as single-chain forms designated F$_v$ fragments obtained recombinantly by fusing the genes encoding the light- and heavy-chain variable regions. Antibodies can be monoclonal or polyclonal and can be those produced in response to administration of an antigen without modification, or, since recombinant techniques have become available, modifications to these antibodies are also possible. For example, also included within anti-PTH-rp are chimeric antibodies which contain regions of amino acid sequences derived from different species, as well as modified forms of antibodies generated by one species that have been altered so as to resemble those of another species without altering the antigen specificity. A particularly preferred embodiment of the anti-PTH-rp of the invention includes antibodies produced in response to administration of PTH-rp to transgenic mice whose immune systems have been modified so that human antibodies can be generated.

Anti-PTH-rp can be prepared in a variety of ways. In one approach, a suitable immunogen, such as PTH-rp or a subunit thereof is administered to a vertebrate-capable of an immune response to the immunogen. Particularly preferred subunits of PTH-rp include those in the N-terminal region, in particular positions 1–34. The PTH-rp or subunit used as immunogen should include epitopes characteristic of the particular species PTH-rp for which antibodies are desired. Suitable polyclonal antisera from the immunized animals could be used; however, it is preferred to obtain monoclonal preparations that are reproducible and readily prepared. Such monoclonal preparations can be obtained by immortalizing the antibody-producing cells of the immunized animal and screening for the appropriate immunoreactivity. Immunospecificity can also be ascertained by screening out those hybridomas that secrete antibodies that are cross-reactive with closely related materials such as PTH.

The resulting antibodies can be used per se or fragments of these antibodies can be prepared using standard proteolytic techniques to provide the Fab, Fab', and F(ab')$_2$ fragments. Alternatively, the genes encoding the antibodies may be isolated, for example from the hybridoma, and manipulated to alter the characteristics of the antibody. Using the isolated genes, F$_v$ units can be constructed which contain the light- and heavy-chain variable regions covalently linked in a single peptide unit.

Since it is preferable that the antibodies to be administered have minimal immunogenicity in the subject to be treated, the antibodies may be manipulated to provide the characteristics of the species of the subject in the nonbinding portions. Construction of chimeric antibodies that contain the constant regions of the desired species is well known; further, techniques are available in the art to modify the antibody primary sequence so as to correspond more closely to the species to be treated.

A number of approaches to do this, for example to "humanize" murine antibodies, are known. In general, these involve engineering the variable region-encoding portions of the gene so that the complementarity-determining regions (CDRs) are left intact while the framework regions (FRs) are modified to match those of the desired species. A particularly preferred way to obtain antibodies immunoreactive with PTH-rp and having human characteristics is through immunization of a transgenic animal which animal responds to administration of antigen by producing human antibodies rather than antibodies with the characteristics of endogenous immunoglobulins. Such transgenic animals are described, for example, in PCT Application WO91/10741, incorporated herein by reference.

The appropriate antibodies or other forms of anti-PTH-rp are formulated for administration in a manner customary for administration of such materials. Typical formulations are those provided in *Remington's Pharmaceutical Sciences,* latest edition, Mack Publishing Company, Easton, Pa. Preferably, the anti-PTH-rp is administered by injection, including intramuscular, intravenous, subcutaneous or peritoneal injection. However, other modes of administration may also be used provided means are available to permit the anti-PTH-rp to enter the systemic circulation, such as transmucosal or transdermal formulations, which can be applied as suppositories, skin patches, or intranasally. In addition, local administration such as by cerebrospinal injection or local injection into the bone metastasis sites or fracture sites may also be used. Any suitable formulation which effects the transfer of the anti-PTH-rp to the bloodstream or locally to the bone may properly be used.

For injection, suitable formulations generally comprise aqueous solutions or suspensions using physiological saline, Hank's Solution, or other buffers optionally including stabilizing agents or other minor components. Liposomal preparations and other forms of microemulsions can also be used. The anti-PTH-rp may also be supplied in lyophilized form and reconstituted for administration. Transmucosal and transdermal formulations generally include agents which facilitate transition of the mucosal or dermal barrier, such as bile salts, fusidic acid and its analogs, various detergents, and the like. Oral administration would also be possible provided suitable enteric coatings can be formulated to permit the anti-PTH-rp to survive the digestive tract.

The nature of the formulation will depend to some extent on the nature of the anti-PTH-rp chosen and a suitable formulation is prepared using known techniques and principles of formulation well known to those in the art. The percentage of anti-PTH-rp contained in a particular pharmaceutical composition will also depend on the nature of the formulation; the percentage of anti-PTH-rp will typically vary over a wide range from about 1% by weight to about 85% by weight.

The appropriate dosage level will also vary depending on a number of factors including the nature of the subject to be treated, the particular nature of the condition to be treated and its severity, the nature of the anti-PTH-rp used as active ingredient, the mode of administration, the formulation, and the judgment of the practitioner. Generally, dosages will be in the range of 50 $\mu$g/kg–50 mg/kg, preferably 1 mg/kg–10 mg/kg at a single dosage. Repeated administration may be required according to protocols to be determined considering the variables set forth above. Typically, daily administration over a period of 3–10 days may be required or administration by intravenous means may be continuous. For chronic conditions, administration may be continued for longer periods as necessary.

As described herein, the subjects who would benefit from administration of the anti-PTH-rp are those who show metastasis of cancer cells to bone or the growth of cancer cells in bone or osteolysis. These patients may or may not have elevated levels of PTH-rp circulating in the blood, unlike those subjects whose hypercalcemia is mediated by the humoral system. As set forth in Japanese Patent Application 4-228089, laid open Aug. 18, 1992, hypercalcemia associated with malignant tumors can be caused either by the accelerated bone resorption by invasion of tumor cells into the bone (local osteolytic hypercalcemia (LOH)) or by the systemic effect of PTH-rp (humoral hypercalcemia of malignancy (HHM)). According to this disclosure, the major examples of hypercalcemia caused by LOH are those resulting from bone metastases of multiple myeloma, breast cancer and the like and examples of hypercalcemia resulting from HHM is the condition associated with squamous cell carcinoma and renal/urological cancers. However, this application does not disclose the relevance of PTH-rp to local osteolytic hypercalcemia.

This distinction between HHM and the metastasis/osteolysis (which may or may not result in hypercalcemia) that is the target of the anti-PTH-rp treatment described herein and the relevance of PTH-rp to such metastasis/osteolysis is clearly demonstrated in the murine model system described by the present inventors in Nakai et al. (supra). Two tumor cell lines were used in this model: RWGT-2 which is a human squamous cell carcinoma of the lung that produces large amounts of PTH-rp in culture (251±8 pM) and MDA231, the human breast adenocarcinoma described above that produces low amounts in vitro (3.1±0.3 pM). The cultured tumor cells were inoculated by intramuscular ($10^7$ cells) or intracardiac injection ($10^5$ cells) into athymic nude mice. The levels of calcium ion in blood and of PTH-rp in plasma were measured, along with obtaining skeletal radiographs and bone histology.

Mice inoculated intramuscularly with either cell line developed local tumors in three weeks without metastases. Mice bearing RWGT-2 developed hypercalcemia (2.44±0.16 mM calcium) with increased PTH-rp (11.8±2.2 pM). Mice bearing MDA231 remained normal calcemic (1.22±0.03 mM) and PTH-rp was not increased in the plasma (0.69±0.17 pM). Osteoclastic bone resorption occurred in the RWGT-2-bearing mice, but not in MDA231-bearing mice.

On the other hand, mice inoculated in the left ventricle with either cell line developed osteolytic lesions in 4 weeks. MDA231-bearing mice remained normal calcemic (1.22±0.03 mM) as did mice bearing RWGT-2 (1.45±0.19 mM). PTH-rp concentration in the plasma was not increased in the MDA231-bearing mice (0.88±0.15 pM) and only slightly increased in RWGT-2-bearing mice (2.75±2.68 pM). However, tumor was present adjacent to areas of increased osteoclastic bone resorption in both groups.

Thus, the authors conclude that PTH-rp causes different syndromes depending on where it is produced; when produced by tumors at a distant site from bone at high levels (RWGT-2), plasma PTH-rp is increased and hypercalcemia occurs without metastatic bone disease. They state that when PTH-rp is produced locally by tumor cells in bone (MDA231) localized bone destruction, with or without hypercalcemia, occurs without necessarily an increase in circulating PTH-rp. On the other hand, the observed osteolysis could be caused in part by PTH-rp released by other cells in response to signals from the metastasized cancer; in addition, enhanced levels of PTH-rp may be produced by the metastasized cancer cells when in the environment of the bone matrix. It is nevertheless clear that the syndrome addressed by the method of the present invention is clearly different from HHM.

Subjects afflicted with conditions responsive to the method of the invention can readily be identified. In some cases, the nature of the disease itself is diagnostic. Endogenous osteolytic conditions such as osteoporosis, osteomalacia, renal osteodystrophy and Paget's Disease are routinely diagnosed. The presence of osteolysis in general can be verified by ascertaining the presence of bone lesions using x-ray scans. Generally speaking, subjects who are diagnosed with cancers of bone origin or cancers which have metastasized to bone or which have the prognosis for metastasis to bone are suitable subjects. The prognosis may be made on the basis of the known nature of the tumor which can be ascertained by biopsy and classification, or may be determined independently by assaying a biopsied tumor for its capacity to produce PTH-rp at elevated levels in the presence of components associated with bone. As stated above, the present inventors have shown that the metastatic tumor MDA231 produces increased levels of PTH-rp when the cells are cultured on an extracellular matrix produced by bone cells.

Thus, by a variety of criteria, a subject exhibiting the particular syndrome treatable by the method of the invention may be ascertained.

The benefits of the treatment described herein are manifest. In addition to the direct effect of the anti-PTH-rp in reducing bone metastasis and the associated bone lesions, the secondary effects of the metastases and bone lesions are also addressed. Thus, subjects exhibiting metastasis and osteolysis may secondarily exhibit hypercalcemia due to the destruction of the bone; the fractured or weakened bones resulting from osteolysis may compress the neural networks in their immediate vicinity ultimately resulting in paralysis or paraplegia; the risk of pathologic fracture is obvious; cachexia can often result; and bone destruction is inevitably associated with pain. All of the foregoing directly or indirectly decrease survival prognosis. Mitigation of these negative effects results from the prevention and treatment of cancer metastasis to the bone environment by cancers originating from either bone or other tissues; from the prevention and treatment of cancer growth on the bone and from the resulting prevention and treatment of the bone lesions caused by the foregoing. The anti-PTH-rp which lies at the heart of the method of the present invention represents a successful focus of treatment despite the multiplicity of factors that have been suggested to be responsible for the symptomology described herein.

The following examples are intended to illustrate but not to limit the invention.

PREPARATION A

Effect of PTH-rp Monoclonal Antibody on Calcium Levels in an HHM Model

To confirm the effect of anti-PTH-rp in lowering calcium levels in HHM, mice were injected subcutaneously or intravascularly with either CHOK-1 cells or with bone-seeking squamous lung cancer cells designated RWGT-2 on day 0. For injection, the mice were under anesthesia with 0.05 mg/g pentobarbital. The cells ($1\times10^5$) were suspended in 0.1 ml PBS. On days 19 and 20 the mice received either 0.3 ml PBS or 0.3 ml containing 75 µg anti-PTH-rp (1–34) monoclonal antibodies (Sato et al. *J Bone Min Res* (1993) 8:849–860) subcutaneously.

Calcium levels in the plasma were measured at days 0, 7, 14, 17, 19 and 21. For the measurement, the mice were anesthetized and calcium ion was determined using a Ciba-Corning calcium pH analyzer (Model 634, Corning, Medfield, Mass.) as described by Yoneda, T. et al. *J Clin Oncol* (1991) 9:468–477.

The results are shown in FIG. 1. As shown, the control mice implanted with CHOK-1 cells maintain normal calcium levels. Mice bearing RWGT-2 show continuously increasing calcium levels (solid circles) when only PBS is administered while administration of the anti-PTH-rp dramatically lowers the calcium levels in the blood of mice receiving antibody (solid triangles). Thus, in this HHM model, anti-PTH-rp controls hypercalcemia mediated by circulating PTH-rp.

EXAMPLE 1

Effect of Anti-PTH-rp on Bone Resorption Stimulated by Various Agents

Figure 2:
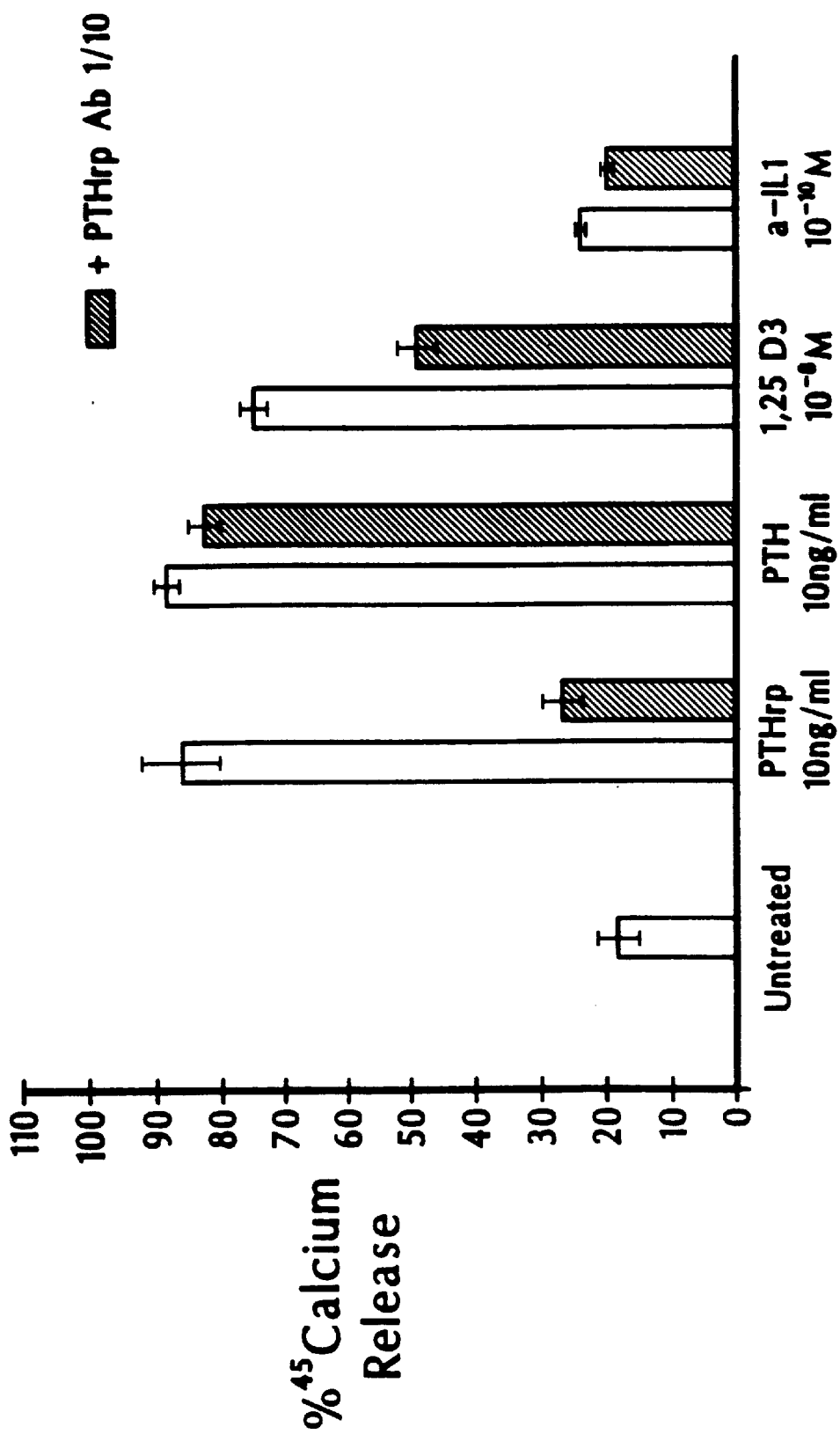
FIG. 2 is a graph showing the effect of monoclonal antibodies specific for PTH-rp on calcium release in bone resorption stimulated by PTH-rp, PTH, or IL-1 in an organ culture model.

In this example, the percentage of labeled calcium ($^{45}$Ca) from fetal rat long bone was used as a measure of bone resorption. To label the bones, pregnant female rats at the 18th day of gestation were injected subcutaneously with 50 µCi of labeled calcium salt. The embryos were harvested the next day, at 19 days gestation, and long bones were obtained from the fetuses. The bones were cultured in standard media for 120 hours in the presence or absence of various putative bone resorption stimulation factors and in the presence and absence of the anti-PTH-rp (1–34) antibody used in Preparation A. The results are shown in FIG. 2.

As shown, untreated bones released roughly 20% of the labeled calcium into the medium over the 120-hour time frame. The addition of 10 ng/ml of PTH-rp to the culture medium results in release of almost 90% of labeled calcium; however, addition of anti-PTH-rp antibodies diminishes this to roughly 30%. Addition of 10 ng/ml PTH itself to the medium also results in almost 90% release of the calcium indicator of bone resorption but the antibody is sufficiently immunospecific to PTH-rp that there is essentially no effect by virtue of the presence of this antibody. The antibody also appeared to diminish the calcium release stimulated by 1,25 D-3 present at $10^{-8}$ M, however, these results could not be repeated. The addition of αIL-1 at $10^{-10}$ M had little effect on calcium release and the addition of the antibody was also without effect.

EXAMPLE 2

Effect of Anti-PTH-rp on Long Bone Lesions

The osteolytic/metastatic model of Nakai, M. et al. *Cancer Res* (1992) 52:5395–5399 was used. MDA231+4 cells were injected into the left ventricle with the mice under anesthesia with 0.05 mg/g pentobarbital on day 0. On days 14, 17 and 20, 0.3 ml anti-PTH-rp (1–34) containing 75 µg protein or 0.3 ml PBS was injected subcutaneously. The area of bone lesions was estimated on radiographs; the mice were anesthetized deeply, laid down in prone position against the films (22×27 cm X-O Mart AR Kodak, Rochester, N.Y.) and exposed with an x-ray at 35 kvp for 6 seconds using a Faxtron Radiographic Inspection Unit (Model 8050-020, Field Emission Corporation, Inc., McMinnville, Oreg.). Films were developed using an RPX-O Mart Processor (Model M8B, Kodak). All radiographs were evaluated extensively by three different individuals. Metastatic foci, recognized as demarcated radiolucid lesions in bones, were enumerated. At the end of the experiment, the mice were sacrificed and bones were fixed in buffered 10% formalin and decalcified to confirm the presence of metastatic tumor and to examine the relationship between tumor and the related bones.

Figure 3:
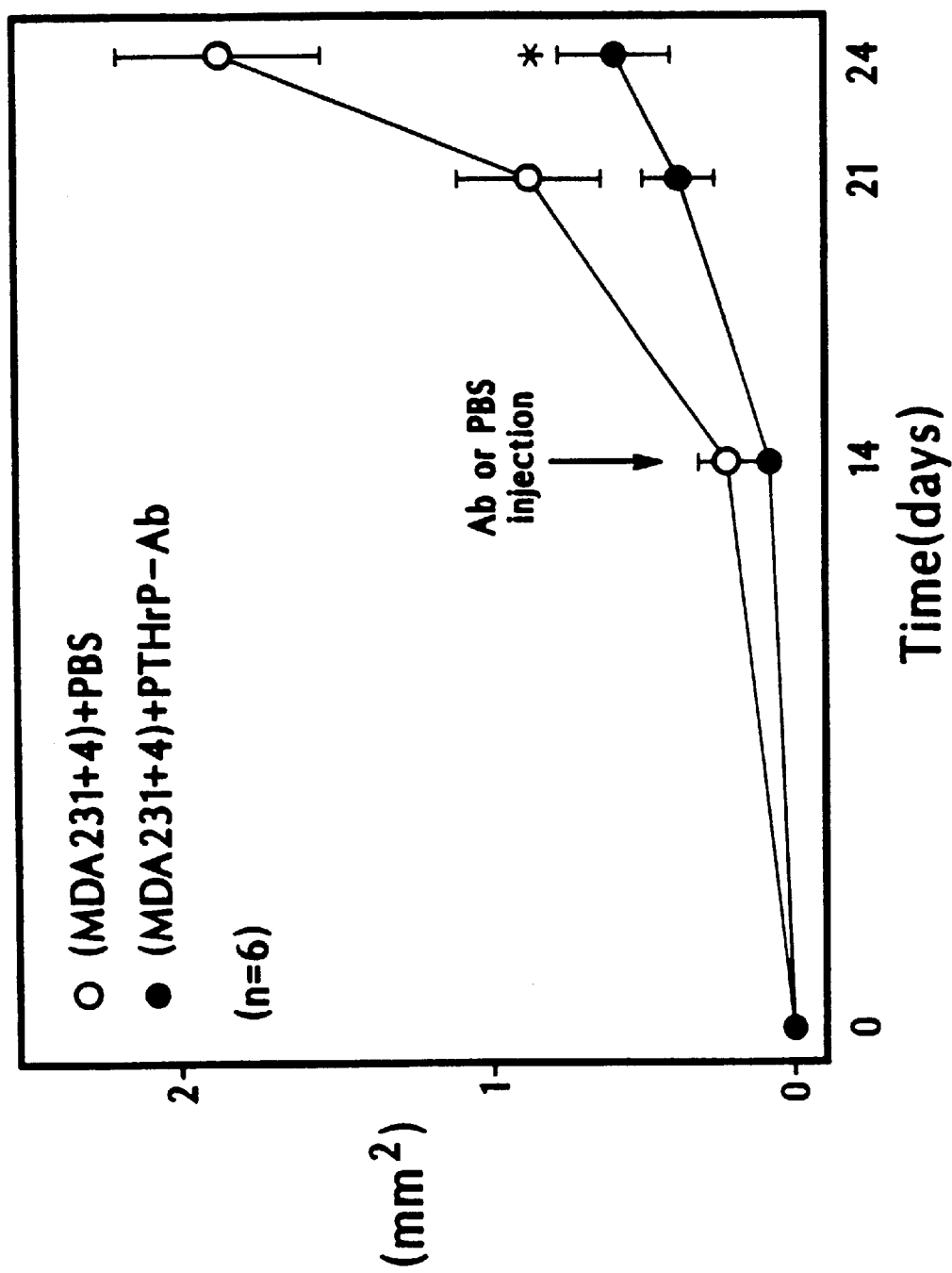
FIG. 3 is a graph showing the effect of administering anti-PTH-rp antibodies on the total area shown to be associated with bone lesions by x-ray diagnosis in tumor-bearing mice.

The results were tabulated as total lesion area in the bones of the fore- and hind-limbs and are shown as calculated for a single bone in FIG. 3. As indicated, the total lesion area in a single bone, shown on the y-axis, is diminished when anti-PTH-rp is administered and is statistically significantly decreased at day 24.

EXAMPLE 3

Osteoporosis Model

Ovariectomized female rats are used as a model of osteoporosis. Bone loss is quite rapid: in the tibial metaphysis, 80% of the secondary spongiosa is lost over 3 months; loss in the vertebrae is only slightly slower. The rats may be studied in the acute phase of bone loss following ovariectomy or some months later, depending on whether the aim is to block bone loss or to stimulate recovery of lost bone.

One week after ovariectomy or sham surgery, 250-gram Sprague-Dawley rats are given either PBS, control antibodies, anti-PTH-rp (1–34) or estrogen over a period of 28 days with the injections administered under methoxyflurane anesthesia. Prior to sacrifice, rats are administered single doses of tetracycline and then demeclocycline in order to assess rates of mineralization. After euthanasia, the tibia and lumbar vertebrae are removed, fixed and processed for histomorphometric evaluation of decalcified and undecalcified sections.

Bone mineral density and assessment of bone mass are determined by dual energy x-ray absorptiometry. The animals administered anti-PTH-rp, but not the animals receiving PBS or control antibodies, show a decrease in bone loss.

We claim:

1. A method of decreasing bone loss associated with a non-metastatic endogenous disease condition, which method comprises:

administering to a subject in need of such treatment an amount of antibodies that specifically bind to PTH-rp or a binding fragment thereof selected from the group consisting of Fab, Fab', $F(ab')_2$ and $F_v$ sufficient to effect said decrease in bone loss.

2. The method according to claim 1, wherein said non-metastatic endogenous disease condition is selected from the group consisting of: osteoporosis, osteomalacia, renal osteodystrophy and Paget's disease.

3. The method according to claim 1, wherein said non-metastatic endogenous disease condition is osteoporosis.

4. The method according to claim 1, wherein said method further results in ameliorating at least one symptom associated with said disease.

5. The method according to claim 4, wherein said symptom is selected from the group consisting of:

that wherein said subject is suffering from pain and said decreasing bone loss alleviates said pain;

that wherein said subject is at risk for neural compression and said decreasing bone loss avoids or alleviates said compression;

that wherein said subject is hypercalcemic and said decreasing bone loss results in amelioration of said hypercalcemia;

that wherein said subject is at risk for mortality and said decreasing bone loss lengthens survival time;

that wherein said subject is at risk for pathologic fractures and said decreasing bone loss lessens said risk;

that wherein said subject is cachexic and said decreasing bone loss ameliorates said cachexia; and combinations of the foregoing.

6. A method of decreasing bone loss resulting from osteoporosis, said method comprising:

administering to a subject in need of such treatment an amount of antibodies that specifically bind to PTH-rp or a binding fragment thereof selected from the group consisting of Fab, Fab', $F(ab')_2$ and $F_v$ sufficient to effect said decrease in bone loss.

7. A method to identify and treat subjects suffering from osteoporosis, said method comprising:

determining whether said subject has osteoporosis; and administering to a subject thus identified an amount of antibodies that specifically bind to PTH-rp or a binding fragment thereof selected from the group consisting of Fab, Fab', $F(ab')_2$ and $F_v$ sufficient to decrease bone loss resulting from said osteoporosis.

8. The method according to claim 7, wherein said determining comprises ascertaining the presence of bone lesions using x-ray scans.

* * * * *